United States Patent
Kim et al.

(10) Patent No.: US 8,597,572 B2
(45) Date of Patent: Dec. 3, 2013

(54) AUTOMATIC ANALYZING METHOD AND APPARATUS FOR MICROFLUIDIC SYSTEM

(75) Inventors: Su-hyeon Kim, Seoul (KR); Yoon-kyoung Cho, Suwon-si (KR); Jeong-gun Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1081 days.

(21) Appl. No.: 12/128,680

(22) Filed: May 29, 2008

(65) Prior Publication Data

US 2009/0099782 A1 Apr. 16, 2009

(30) Foreign Application Priority Data

Oct. 10, 2007 (KR) .................. 10-2007-0102139

(51) Int. Cl.
*G01N 33/50* (2006.01)
(52) U.S. Cl.
USPC .............. 422/72; 702/19; 702/44; 702/160; 702/182; 702/142; 702/149; 702/187; 702/188; 422/101; 422/63; 436/43
(58) Field of Classification Search
USPC ........ 702/72, 19; 422/566, 504, 400, 506, 81, 422/72, 502, 68.1, 63; 324/214; 436/177, 436/180, 50, 43; 705/2
See application file for complete search history.

(56) References Cited

U.S. PATENT DOCUMENTS

| | | | |
|---|---|---|---|
| 6,174,675 B1 * | 1/2001 | Chow et al. ................. | 435/6.19 |
| 6,246,966 B1 * | 6/2001 | Perry ............................. | 702/91 |
| 6,366,924 B1 * | 4/2002 | Parce .............................. | 1/1 |
| 6,647,397 B2 * | 11/2003 | Parce ............................. | 422/67 |
| 7,024,281 B1 * | 4/2006 | Unno ............................ | 700/275 |
| 7,026,131 B2 * | 4/2006 | Hurt et al. .................... | 435/7.25 |
| 7,087,203 B2 * | 8/2006 | Gordon et al. ................ | 422/72 |
| 7,155,344 B1 * | 12/2006 | Parce et al. .................. | 702/19 |
| 7,476,361 B2 * | 1/2009 | Kellogg et al. ............... | 422/72 |
| 7,951,332 B2 * | 5/2011 | Cho et al. ..................... | 422/72 |
| 8,010,808 B2 * | 8/2011 | Choi et al. .................... | 713/193 |
| 2001/0055812 A1 * | 12/2001 | Mian et al. .................... | 436/45 |
| 2002/0076354 A1 * | 6/2002 | Cohen ............................ | 422/72 |
| 2002/0098528 A1 * | 7/2002 | Gordon et al. ............... | 435/7.21 |
| 2003/0224457 A1 * | 12/2003 | Hurt et al. ..................... | 435/7.2 |
| 2005/0148084 A1 * | 7/2005 | Parce et al. .................. | 436/50 |
| 2006/0024831 A1 * | 2/2006 | Kao et al. ........................ | 436/8 |
| 2006/0270064 A1 * | 11/2006 | Gordon et al. ................ | 436/518 |
| 2007/0067120 A1 * | 3/2007 | Kasselmann et al. ........... | 702/57 |
| 2007/0077605 A1 * | 4/2007 | Hurt et al. .................... | 435/7.21 |
| 2008/0058192 A1 * | 3/2008 | Cho et al. ........................ | 494/1 |
| 2008/0177518 A1 * | 7/2008 | Krishnamoorthy et al. ...... | 703/9 |

OTHER PUBLICATIONS

Korean Intellectual Property Office, Communication dated Jun. 27, 2013 issued in a counterpart KR application No. 10-2007-0102139.

* cited by examiner

*Primary Examiner* — Carol S Tsai
(74) *Attorney, Agent, or Firm* — Sughrue Mion, PLLC (57) ABSTRACT

Provided are an automatic analyzing method and apparatus for a microfludic system. The apparatus includes means for recognizing a disc or chip in the microfludic system, performs an operation and detection by automatically loading a DB according to a recognized type, and perform quantization of a test.

17 Claims, 6 Drawing Sheets

| Sequence_ID | Main_Function | Motor | | | | | | Laser | | | |
|---|---|---|---|---|---|---|---|---|---|---|---|
| | | Action | Speed | Direction | Acceleration | Time | Repetition | Laser_Home | Distance | Angle | Laser_Time |
| 1 | Blood Metering | Spin | 1800 | CW | 1 | 20 | | | | | |
| 2 | Wait | Wait | | | | 1 | | | | | |
| 3 | Serum Separation 1 | Spin | 3600 | CW | 5 | 80 | | | | | |
| 4 | Wait | Wait | | | | 2.5 | | | | | |
| 5 | Serum Separation 2 | Spin | 3600 | CCW | 5 | 80 | | | | | |
| 6 | Wait | Wait | | | | 2.5 | | | | | |
| 7 | Transfer serum to Mix 1 | Transfer | 2400 | CCW | 2 | 15 | | | 8.1 | 86.7 | 5 |
| 8 | Wait | Wait | | | | 1.5 | | | | | |
| 9 | Transfer serum to Mix 2 | Transfer | 3600 | CW | 5 | 15 | | | 12.3 | 93.7 | 5 |
| 10 | Wait | Wait | | | | 2.5 | | | | | |
| 11 | Mixing | Vibration | 2400 | | 2 | 5 | 4 | | | | |
| 12 | Wait | Wait | | | | 1.5 | | | | | |
| 13 | Open Mix 1 | Transfer | 3600 | CCW | 5 | 20 | | | 23 | 53.9 | 5 |
| 14 | Wait | Wait | | | | 2.5 | | | | | |
| 15 | Open Mix 2 | Transfer | 3600 | CCW | 5 | 30 | | | 24 | 169.8 | 5 |
| 16 | Wait | Wait | | | | 2.5 | | | | | |
| 17 | Transfer Confirm | Spin | 3600 | CW | 5 | 60 | | | | | |
| 18 | Wait | Wait | | | | 2.5 | | | | | |

FIG. 5

| Det_Sequence_ID | Det_Discription | Start_Time | Home_Position | Rotation_Angle | Detection_Method | Angle | Repetition |
|---|---|---|---|---|---|---|---|
| 1 | | 60 | Yes | 46.8 | Absorbance | 7.2 | 50 |
| 2 | | 180 | Yes | 46.8 | Absorbance | 7.2 | 50 |
| 3 | | 300 | Yes | 46.8 | Absorbance | 7.2 | 50 |

FIG. 6

| Test_ID | Test_Name | Display_Name | Test_Version | Create_Date | Test_Discription | Unit |
|---|---|---|---|---|---|---|
| Chem01 | Alkaline phosphatase | ALP | 1.0 | 2007. 05. 27 | | IU/L |
| Chem02 | Alanine Aminotransferase | ALT | 1.0 | 2007. 05. 27 | | IU/L |
| Chem03 | Amylase | AMY | 1.0 | 2007. 05. 27 | | IU/L |
| Chem04 | Aspartate Aminotransferase | AST | 1.0 | 2007. 05. 27 | | IU/L |
| Chem05 | Urea Nitrogen | BUN | 1.0 | 2007. 05. 27 | | mg/dl |
| Chem06 | Total Cholesterol | Chol | 1.0 | 2007. 05. 27 | | mg/dl |
| Chem07 | Creatine Kinase | CK | 1.0 | 2007. 05. 27 | | IU/L |
| Chem08 | Direct Bilirubin | DBIL | 1.0 | 2007. 05. 27 | | mg/dl |
| Chem09 | Gamma Glutamyl Transferase | GGT | 1.0 | 2007. 05. 27 | | IU/L |
| Chem10 | Glucose Oxidase | GLU | 1.0 | 2007. 05. 27 | | mg/dl |
| Chem11 | Lactate Dehydrogenase | LD | 1.0 | 2007. 05. 27 | | IU/L |
| Chem12 | Total Bilirubin | TBIL | 1.0 | 2007. 05. 27 | | mg/dl |
| Chem13 | Triglycerides | TRIG | 1.0 | 2007. 05. 27 | | mg/dl |
| Chem14 | Uric Acid | UA | 1.0 | 2007. 05. 27 | | mg/dl |

| Test_ID | Alt_Unit | Normal_Max | Normal_Min | Calculation | Assay_Type | Coefficient |
|---|---|---|---|---|---|---|
| Chem01 | | 117 | 39 | (log(#010217/#010201)−log(#020217/#020201)) | Kinetic | 3608.893 |
| Chem02 | | 35 | 5 | (log(#010104 /#010101)−log(# 020104 /#02 0101)) | Kinetic | −2021.09 |
| Chem03 | | 110 | 10 | (log(#010218/#010201)−log(#020218/#020201)) | Kinetic | 5468.242 |
| Chem04 | | 40 | 5 | (log(#010103/#010101)−log(#020103/#020101)) | Kinetic | −1287.82 |
| Chem05 | | 20 | 8 | (log(#010114/#010101)−log(#020114/#020101)) | Kinetic | −199.965 |
| Chem06 | | 250 | 130 | log(#030401/#030420) | End Point | 1563.805 |
| Chem07 | | 195 | 24 | (log(#010115/#010101)−log(#020115/#020101)) | Kinetic | 1609.153 |
| Chem08 | | 0.5 | 0 | log(#030501/#030506)*M05 | End Point | 4.662 |
| Chem09 | | 50 | 0 | (log(#010205/#010201))− | Kinetic | 651.111 |
| Chem10 | | 110 | 70 | log(#030401/#030419) | End Point | 339.462 |
| Chem11 | | 360 | 160 | (log(#010116/#010101)−log(#020116/#020101))*#M05 | Kinetic | −16840.9 |
| Chem12 | | 1 | 0.1 | log(#030501/#030521) | End Point | 12.989 |
| Chem13 | | 155 | 50 | log(#030501/#030522) | End Point | 643.932 |
| Chem14 | | 6.9 | 3.9 | | End Point | 90.143 |

FIG. 7

AUTOMATIC ANALYZING METHOD AND APPARATUS FOR MICROFLUIDIC SYSTEM

CROSS-REFERENCE TO RELATED PATENT APPLICATION

This application claims the benefit of Korean Patent Application No. 10-2007-0102139, filed on Oct. 10, 2007, in the Korean Intellectual Property Office, the disclosure of which is incorporated herein in its entirety by reference.

BACKGROUND OF THE INVENTION

1. Field of the Invention

The present invention relates to an automatic analyzing method and apparatus for a microfludic system, and more particularly, to an automatic analyzing method and apparatus for automatically performing operations, detection, and in data processing for a microfludic system.

2. Description of the Related Art

In general, a microfludic structure performing an independent function in a microfludic system includes a chamber for holding back a fluid, a channel for flowing the fluid through, and a valve for controlling the flow of the fluid, and can be made by variously combining the parts. A lap-on-a-chip is a device for performing several steps of processing and operations by embedding such a microfludic structure on a chip type substrate in order to perform tests, such as a biochemical reaction test, on a small-sized chip.

In order to carry a fluid in a microfluidic structure, a driving force is necessary, and for the driving force, a capillary force, electroosmotic force, or a force generated by a separate pump may be used. Recently, disc-type microfluidic devices for performing a series of jobs by embedding a microfluidic structure on a disc-type platform and flowing a fluid using a centrifugal force have been suggested. Such a disc-type microfluidic device is called a lab compact disc (CD) or a lab-on-a-disc. Efforts for providing various disc-type microfluidic devices for quickly and accurately performing a job needed in a disc type platform based on the centrifugal force are progressing.

According to the development of microfluidic device technology, miniaturized devices, such as a lab-on-a-chip and a lab-on-a-disc, for replacing complex systems needed to automate processes from sample pre-processing to result analysis have been developed. Adding to the development of the miniaturized devices, it is also important that the miniaturized devices are automated for user convenience and safety.

In order to deal with various kinds of samples with a single device, different sample pre-processing processes may exist, and operations according to the processes are different as well. In addition, a plurality of analytes in a sample can be analyzed at the same time. For example, when a biochemical test of blood is performed, 4 to more than 10 biochemical substances can be analyzed with a disc, a set of testing items which can be analyzed at the same time is called a panel, various types of panels including different testing items may exist, and each panel must be dealt with using a single device.

SUMMARY OF THE INVENTION

The present invention provides an automatic analyzing method and apparatus for a microfludic system, which includes means for recognizing a disc or chip, performs operations and detections by automatically loading a database according to the recognized type, and performs tests.

According to an aspect of the present invention, there is provided an automatic analyzing method for a microfludic system, the method comprising: recognizing a disc of the microfludic system; determining a database (DB) file corresponding to the recognized disc from a DB and loading the determined DB file; performing an operation of the microfludic system according to operation-related information of the loaded DB file; performing detection of the microfludic system according to detection-related information of the loaded DB file; and calculating a detection result value according to test-related information of the loaded DB file and outputting the calculated detection result value.

According to another aspect of the present invention, there is provided an automatic analyzing apparatus for a microfludic system, the apparatus comprising: a recognition unit recognizing a disc of the microfludic system; a first controller controlling an operation and detection of the microfludic system; and a second controller controlling the first controller to control the operation and detection of the microfludic system, by determining a database (DB) file corresponding to the recognized disc, loading the determined DB file from a storage unit storing the DB file, and transmitting information on the loaded DB file to the first controller.

According to another aspect of the present invention, there is provided a computer readable recording medium storing a computer readable program for executing the method.

Details and improvements of the present invention are disclosed in dependent claims.

BRIEF DESCRIPTION OF THE DRAWINGS

The above and other features and advantages of the present invention will become more apparent by describing in detail exemplary embodiments thereof with reference to the attached drawings in which:

FIG. 6 illustrates a table for describing a DB for a test according to an embodiment of the present invention.

DETAILED DESCRIPTION OF THE INVENTION

The present invention will be described in detail by explaining embodiments of the invention with reference to the attached drawings.

Figure 1:
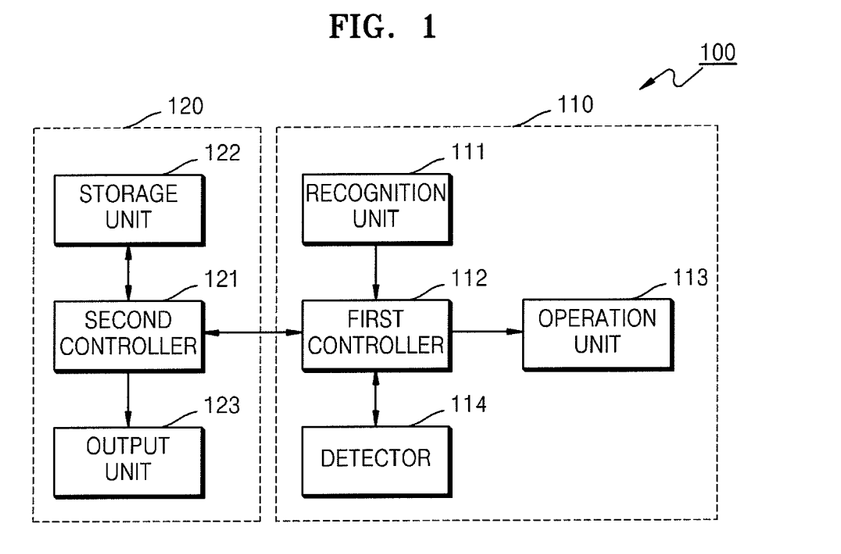
FIG. 1 is a schematic block diagram of an automatic analyzing apparatus for a microfluidic system according to an embodiment of the present invention.

FIG. 1 is a schematic block diagram of an automatic analyzing apparatus 100 for a microfludic system according to an embodiment of the present invention.

Referring to FIG. 1, the automatic analyzing apparatus 100 according to an embodiment of the present invention includes a part 110 controlling operations of a valve and pump of the microfludic system and taking in charge of detection and disc recognition and a part 120 storing a database (DB) for various discs and controlling calculation using the stored DB and an output of the calculation result. The parts 110 and 120 can be configured to communicate with each other. In addition, although the parts 110 and 120 are separated in the drawing, they can be configured in one body.

The part 110 includes a recognition unit 111, a first controller 112, an operation unit 113, and a detector 114.

The recognition unit 111 recognizes a barcode of a disc or a chip by reading the barcode. The recognition unit 111 may be a barcode reader. Even though the barcode is illustrated, the present invention is not limited to the barcode and may include a radio frequency (RF) tag using RFID. Thereby, the recognition unit 111 can recognize identification (ID) information on a disc in a contact or contactless method. The recognition unit 111 provides the ID information recognized from the disc to the first controller 112.

The first controller 112 takes in charge of a general control of the part 110, receives the ID information from the recognition unit 111, and transmits the ID information to a second controller 121. In addition, the first controller 112 controls the operation unit 113 and the detector 114 according to DB information corresponding to the disc ID information received from the second controller 121, receives an operation result and a detection result of the microfludic system from the operation unit 113 and the detector 114, and transmits the operation result and the detection result to the second controller 121.

The operation unit 113 controls an operation of the microfludic system. The operation unit 113 controls a centrifugal force for rotating the disc and an external energy source for opening and closing a valve, e.g., a valve irradiation position of a laser. The operation unit 113 performs jobs, such as pre-processing, concentration, dilution, mixing, and reaction of a sample, by controlling the pump and valve causing the centrifugal force.

The detector 114 detects a reaction result of a sample in the microfludic system. The detector 114 performs the detection by performing an optical reaction in a detection chamber under the control of the first controller 112 based on detection control information received from the second controller 121. The detector 114 transmits a detection result to the second controller 121 via the first controller 112, and the second controller 121 calculates a quantitative value of a biochemical substance of interest in the sample by calculating the detection result and outputs the quantitative value.

The part 120 includes the second controller 121, a storage unit 122, and an output unit 123.

The second controller 121 controls the first controller 112, the storage unit 122, and the output unit 123. That is, the second controller 121 controls a general operation and detection of the microfludic system by controlling the first controller 112, reads a DB file stored in the storage unit 122, and controls an automatic checking operation of the microfludic system based on the read DB file. In more detail, the second controller 121 loads at least one DB file based on barcode information from among DB files stored in the storage unit 122. The second controller 121 may use a separate file for indexing the barcode information and a file name to be loaded from the DB. The second controller 121 performs the jobs, such as pre-processing, concentration, dilution, mixing, and reaction of a sample, by analyzing operation steps in the DB file and controlling the valve and pump with sequential commands.

The storage unit 122 stores information related to operation, detection, and test corresponding to a disc or chip in a DB. The information related to operation includes information on which jobs are performed and variables needed for the jobs, the information related to detection includes information related to operational variables, such as a position detected on a disc and the number of times, in a detection process, and the information related to test includes information regarding an analysis result and information regarding a calculation method.

The DB stores fundamental information and information such as work sequence, detection, and test.

The fundamental information includes a name of a panel, a creation date, and description of the panel. The work sequence includes identification of the work sequence, description of each step, actions containing spin, transfer, laser, vibration, wait, and lysis, and information, such as rotational speed of a rotor, direction including clockwise (CW) and counter clockwise (CCW), acceleration period, deceleration period, and time including second, as variable values needed for each action. The detection includes information, such as identification of the detection, description of the detection, a detection start position, an angle of rotation in the detection, and the number of repetition times in the detection. The test includes a variable needed to identify the test, a test name, an expression used for calculation, calibration needed or not, a value multiplied after calibration, and an expression used for calibration calculation. The information described above can be expressed with a string, a date, and a floating point format.

The information regarding a disc, panel or chip can be inserted into at least one DB file, and a type such as an extensible markup language (XML) can be used for a DB format.

The output unit 123 outputs the quantitative value of a biochemical substance received from the second controller 121.

Since the automatic checking apparatus 100 according to an embodiment of the present invention can modify information regarding operation, detection, and calculation by modifying a DB file without modifying a program when a process is modified or a new diagnosis disc is generated, the automatic checking apparatus 100 can be used by adding or modifying a DB without a program change. A DB file can be stored in a fixed directory designated by a program of the storage unit 122, and a file name can be recorded in a barcode or RFID or stored in the storage unit 122 as a separate list file so that panel information and the file name can be referred to.

Figure 2:
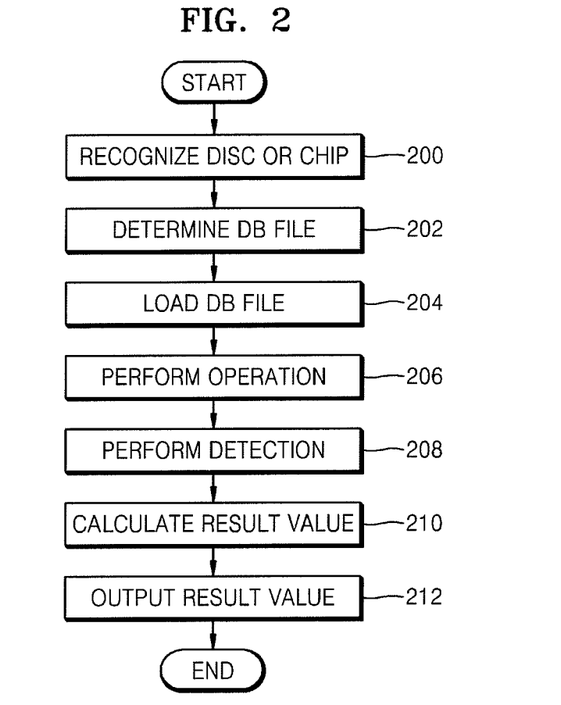
FIG. 2 is a flowchart illustrating an automatic analyzing method for a microfludic system according to an embodiment of the present invention.

FIG. 2 is a flowchart illustrating an automatic checking method for a microfludic system according to an embodiment of the present invention.

Referring to FIG. 2, in operation 200, a disc or chip is recognized by using a recognizable member such as a barcode or RFID in a lab-on-a-disc or lab-on-a-chip. In operation 202, the disc or chip is recognized and a DB file corresponding to the disc or chip is determined. In operation 204, DB file information for performing an operation of the microfludic system is loaded into the DB file. In operation 206, operations, such as sample pre-processing, sample concentration, dilution, mixing, and reaction, by means of jobs, such as pumping and valving, based on the loaded DB file information. In operation 208, detection is performed based on the loaded DB file information and a value read by a detector is stored in a storage unit. In operation 210, a result value is calculated from the data read by the detector and stored in the storage unit by using an expression in a DB. In operation 212, the result value is output. When the result value is output, other information, such as a unit or test name, can be contained in the DB. Since operation or test information is stored in the storage unit in a separate file type instead of a program type, even if a new check is added or a checking method is modified, the checking can be performed by adding or modifying a DB file without a program change.

Since the automatic checking method for a microfludic system according to an embodiment of the present invention automatically performs all of operation, detection, and calculation from a step of recognizing a disc or chip and can perform various operations in one device, the automatic checking method can be used for various types of diagnosis, such as a biochemical check, an immune check, and a deoxyribonucleic acid (DNA) check.

Figure 3:
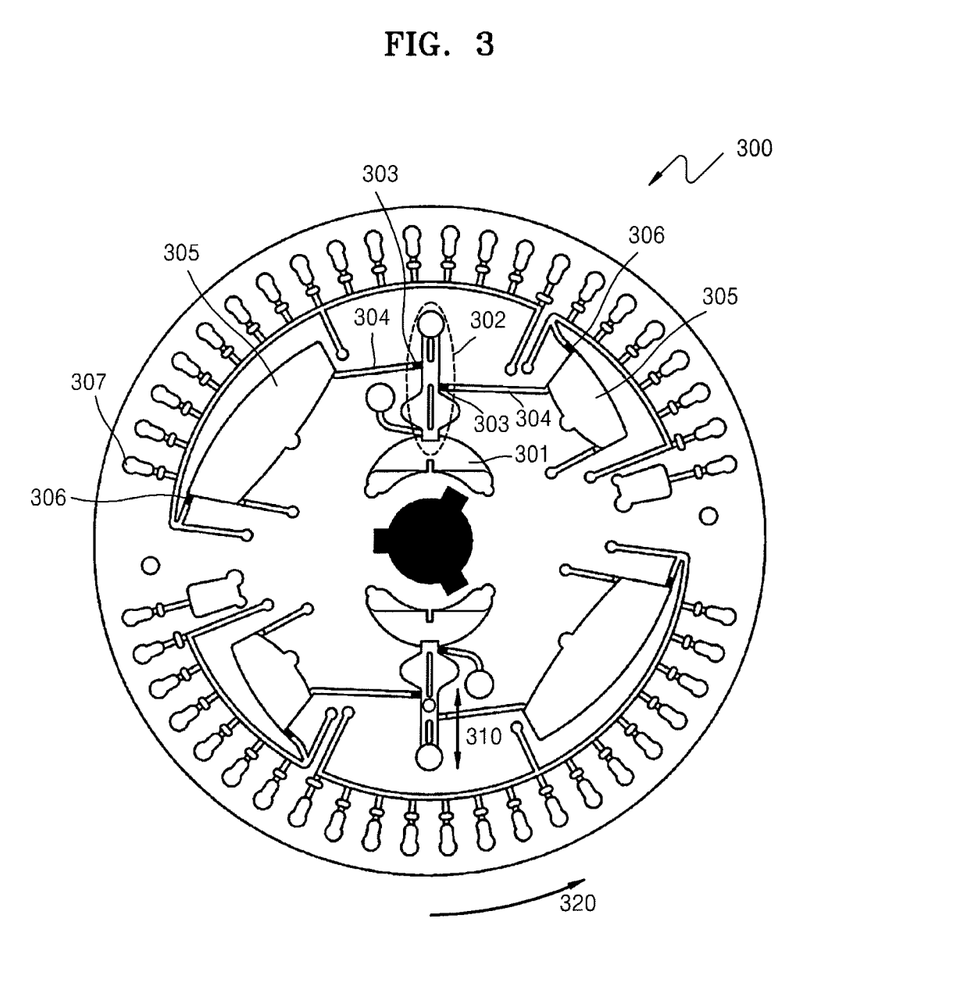
FIG. 3 illustrates a sample analysis disc according to an embodiment of the present invention.

FIG. 3 illustrates a sample analysis disc 300 according to an embodiment of the present invention.

Referring to FIG. 3, the sample analysis disc 300 includes a sample chamber 301, a centrifugation separation unit 302, valves 303, sample distribution channels 304, dilution chambers 305, and detection chambers 307. In addition, reference numeral 310 denotes a movement of a laser to open and close the valves 303, and reference numeral 320 denotes disc rotation for making a fluid flow with a centrifugal force and searching for a position on the sample analysis disc 300.

Operations of the components of the sample analysis disc 300 and an operation of a microfludic system for valve open and close and a sample movement will now be described.

A microfluidic system for quantitating a chemical compound in blood by using a biochemical reaction will now be described as an example. A pump uses the centrifugal force, and a valve is open with a laser. For a correct operation, pumping and valve open/close processes must be sequentially performed. The blood is injected into the sample chamber 301, centrifugation is performed in a high speed in order to separate serum from the blood, and a predetermined amount of sample is sequentially transferred to two dilution chambers 305 by opening the valves 303 with the laser. The sample diluted to two different concentrations is transferred to the detection chambers 306 containing a reagent by opening a subsequent valve 303 and reacted in the detection chambers 307, and the reaction is measured by using extinction. Detailed description of the microfluidic components is disclosed in Korean Patent Application No. 2007-0084522 applied by the applicant.

In order to open the valves 303 and 306, the laser must be irradiated onto positions of the valves 303 and 306, and in this case, an angle 320 of disc rotation and a laser position 310 are important variables. That is, valving and pumping operations at a specific time are sequentially performed by inserting a position for opening each valve into variables of a DB related to the operations. Thus, an automatic check can be correctly performed according to information stored in the DB regardless of a disc type.

Figure 4:
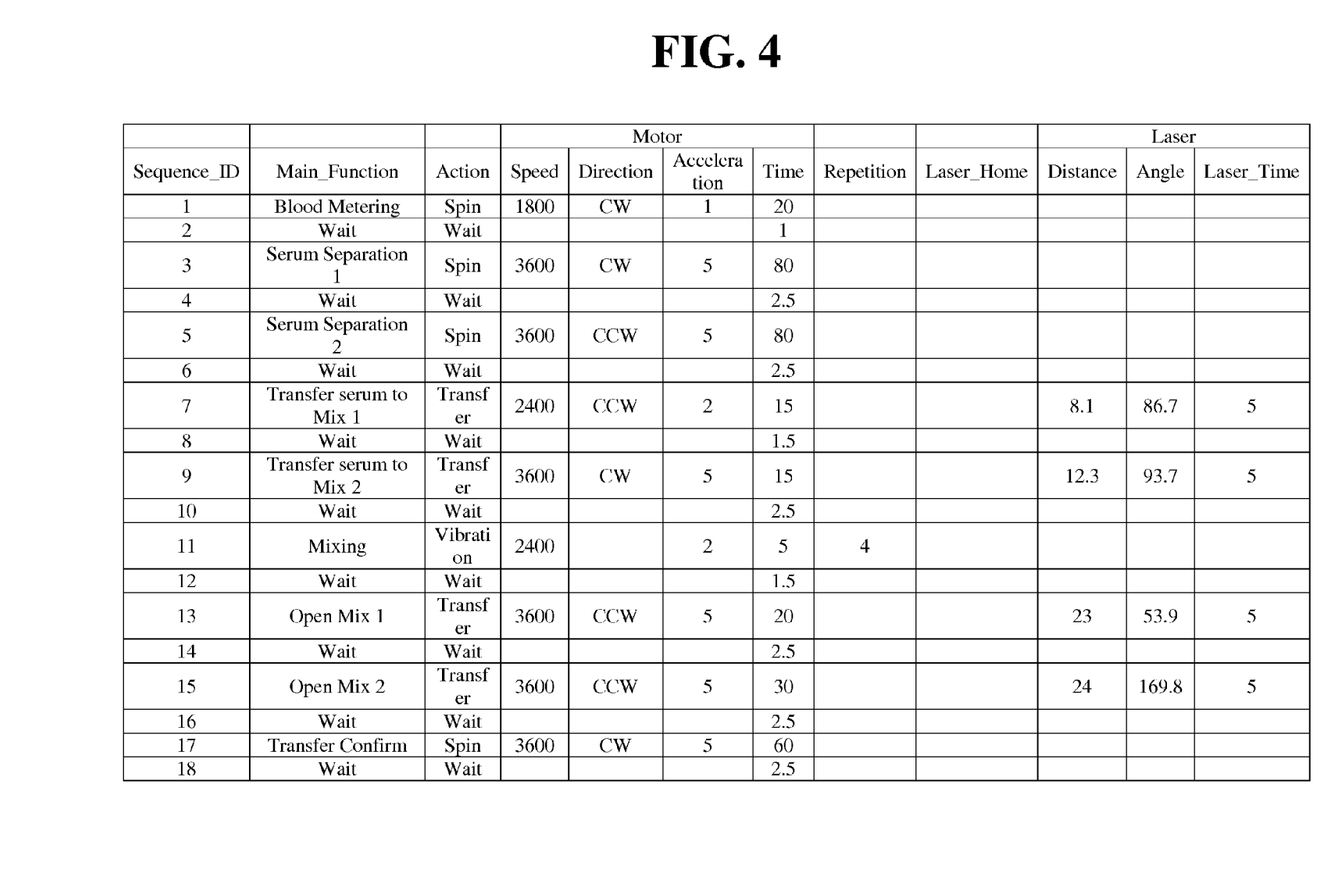
FIG. 4 illustrates a table for describing a database (DB) for a disc operation according to an embodiment of the present invention.

FIG. 4 illustrates a table for describing a DB for a disc operation according to an embodiment of the present invention.

Referring to FIG. 4, an operation of a biochemical checking disc is stored as a DB. The DB related to the operation stores Sequence_ID information, Main_Function information, Action information, Speed, information Direction information, Acceleration information, Time information, Repetition information, Laser_Home information, Distance information, Angle information, and Laser_Time information.

For example, in a case of serum separation, a rotation operation is performed, a motor speed is 3600, a direction is CW, an acceleration is 5, and the operation is performed for 80 seconds. In addition, since Transfer serum to Mix1 is a variable needing a motor and a laser, it is a transfer operation, a motor speed is 2400, a direction is CCW, an acceleration is 2, and the operation is performed for 15 seconds. In addition, for the laser, a moving distance is 8.1, an angle is 86.7, and an irradiation time is 5 seconds.

The second controller 121 controls the first controller 112 to perform a specific function by performing another sub-routine in a program according to an operation based on a loaded DB file and transmitting a command with the variable values described above to the first controller 112. In addition, the variable values can be calculated by the second controller 121 and transmitted to the first controller 112 so that the first controller 112 can easily perform processing.

Figure 5:
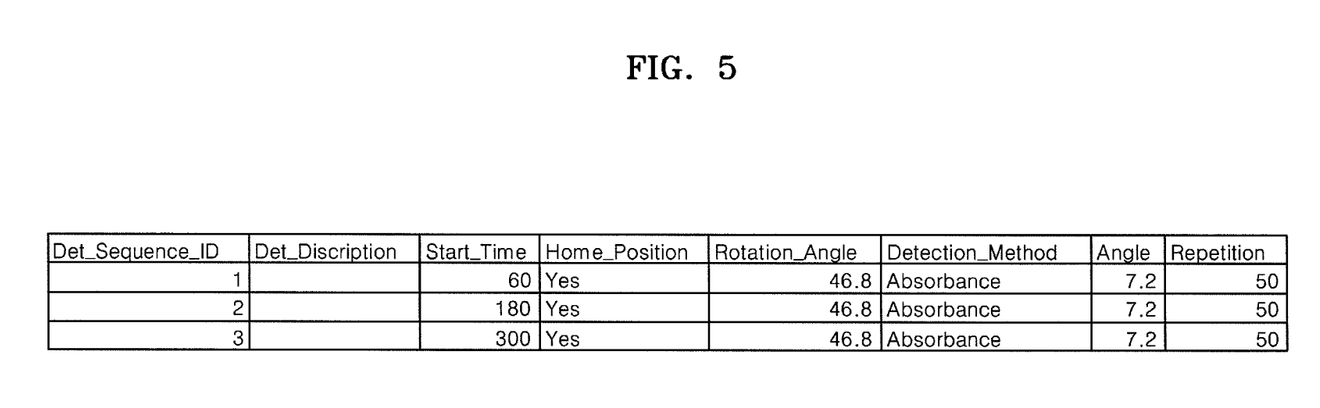
FIG. 5 illustrates a table for describing a DB for detection according to an embodiment of the present invention.

FIG. 5 illustrates a table for describing a DB for detection according to an embodiment of the present invention.

Referring to FIG. 5, a detection operation in a biochemical check is described. The detection operation has a case of needing detection once with an end point and a case of measuring kinetics, such as enzyme quantitation. The latter is a case of performing detection several times at a constant time interval and can be processed by inserting variables in a DB. FIG. 5 illustrates an operation of performing measurement three times at 60, 180, and 300 seconds and performing detection for 50 detection positions having an interval of 7.2°.

FIG. 6 illustrates a table for describing a DB for a test according to an embodiment of the present invention.

FIG. 6 illustrates a DB used to output a test result. A disc or chip can be used for a plurality of detections, and information needed for the detections can be stored in the DB. The DB can include information regarding units, test names, calculation expressions, and coefficients needed for calculations, and each calculation expression can be expressed by calculating a value obtained by penetrating through a sample with absorbance by accessing a value used to obtain a test result from a detection signal. In addition, a compensation coefficient different for each device can be reflected to the calculation.

FIGS. 4 to 6 are edited with Microsoft Excel®, and each table is in a separate worksheet in a file. Each table can be formed so that values of the table can be automatically filled by using Excel functions or an error of variables can be recognized by using functions and conditional expressions. By using a program programmed by a user, an Excel file is transformed to an XML file, the XML file having a text format is stored in the storage unit 122, and when the program is performed, the XML file is read and used by performing parsing.

Figure 7:
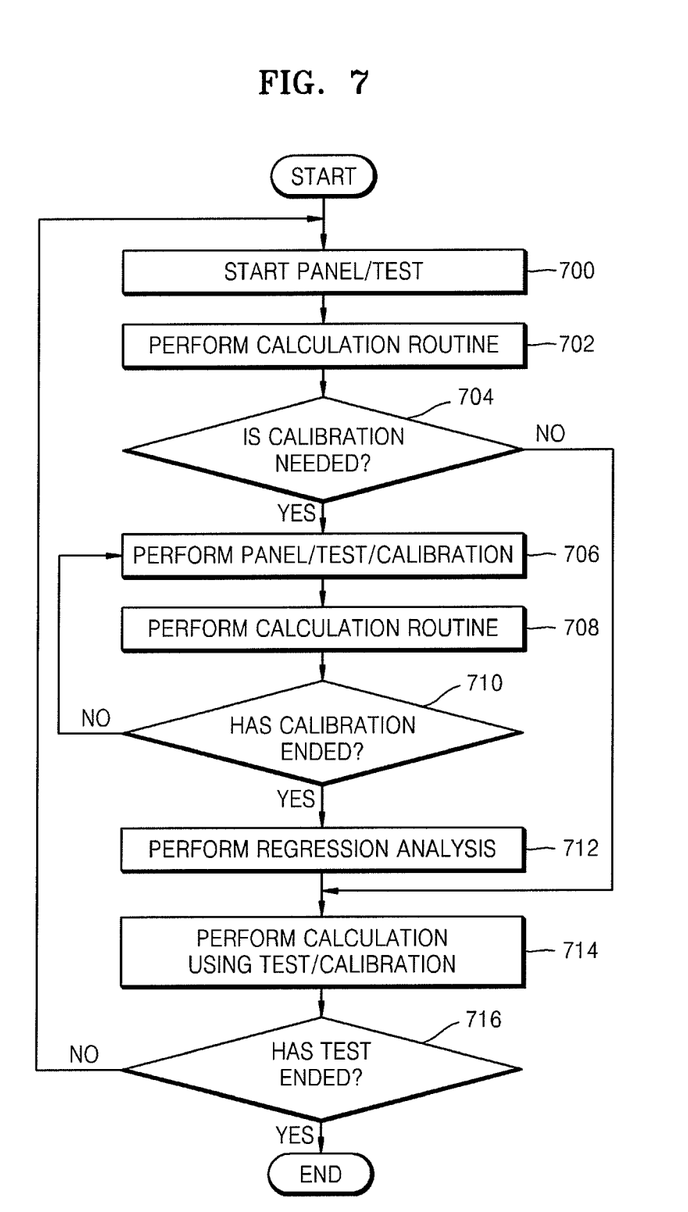
FIG. 7 is a flowchart illustrating a result value calculating method according to an embodiment of the present invention.

FIG. 7 is a flowchart illustrating a result value calculating method according to an embodiment of the present invention.

Referring to FIG. 7, in operation 700, a panel/test loop starts. In operation 702, a calculation routine is performed by using test/calculation expressions of a DB. In operation 704, it is determined in a case where a test/calibration value exists in the DB whether calibration is needed. That is, when a test/calibration value does not exist in the DB, the process proceeds to operation 712, and when a test/calibration value exists in the DB, a test/calibration loop is performed in operation 706. In operation 708, a calculation routine is performed by using test/calibration/calibration calculation expressions of a DB. The calculation routine of operation 708 is the same as that of operation 702. In operation 710, it is determined whether the calibration has ended. If the calibration has ended, regression analysis is performed in operation 712. The regression analysis includes linear regression analysis, and the linear regression analysis will now be described as an example. The linear regression analysis is performed by using a Cal_Calculation value as an X value and a Test/Calibrator/Cal_Concentration value as a Y value, wherein the Test/Calibrator/Cal_Concentration value is a value measured by inserting a calibrator of which concentration is known into a disc, and the Y value is obtained by substituting a value obtained from Test/Calculation for the X value before performing the calibration loop. In operation 714, a result value of the regression analysis is multiplied by a Test/Coefficient value and is compensated to fit a unit. In operation 716, it is determined whether tests have ended. In this case, a loop is performed as many as the number of tests, and the loop ends after all tests ends. That is, if a calculation process ends, a result value for every test is generated.

The embodiments of the present invention can be written as computer programs and can be implemented in general-use digital computers that execute the programs using a computer readable recording medium. Examples of the computer readable recording medium include magnetic storage media (e.g., ROM, floppy disks, hard disks, etc.), optical recording media (e.g., CD-ROMs, or DVDs), and storage media such as carrier waves (e.g., transmission through the Internet). The computer readable recording medium can also be distributed over network coupled computer systems so that the computer readable code is stored and executed in a distributed fashion. Also, functional programs, codes, and code segments for accomplishing the present invention can be easily constructed by programmers skilled in the art to which the present invention pertains.

While this invention has been particularly shown and described with reference to preferred embodiments thereof, it will be understood by those skilled in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. An automatic analyzing method for a microfluidic system, the method comprising:
    recognizing, by an automatic analyzing apparatus for the microfluidic system, a disc of the microfluidic system;
    determining, by the automatic analyzing apparatus, a database (DB) file corresponding to the recognized disc from a DB external to the disc and loading the determined DB file;
    performing, by the automatic analyzing apparatus, an operation of the microfluidic system according to operation-related information read from the loaded DB file;
    performing, by the automatic analyzing apparatus, detection of the microfluidic system according to detection-related information read from the loaded DB file; and
    calculating, by the automatic analyzing apparatus, a detection result value according to test-related information read from the loaded DB file and outputting the calculated detection result value,
    wherein the operation-related information comprises operation-related commands and variables of the microfluidic system.

2. The method of claim 1, further comprising, after the loading, transmitting information for controlling operation, detection, and test of the microfluidic system.

3. The method of claim 1, wherein the DB comprises at least one of fundamental information, work sequence information, detection information, and test information of the disc.

4. The method of claim 1, wherein the detection-related information comprises a detection position and a detection method for the disc in the microfluidic system.

5. The method of claim 1, wherein the test-related information comprises information regarding an analysis result and a calculation method in the microfluidic system.

6. The method of claim 1, wherein the DB has an extensible markup language (XML) format.

7. A non-transitory computer readable recording medium storing a computer readable program for executing the method of claim 1.

8. The method of claim 1, wherein the DB file comprises calibration information indication whether calibration is to performed.

9. An automatic analyzing apparatus for a microfluidic system, the apparatus comprising:
    a recognition unit recognizing a disc of the microfluidic system;
    a first controller controlling an operation and detection of the microfluidic system; and
    a second controller controlling the first controller to control the operation and detection of the microfluidic system, by determining a database (DB) file corresponding to the recognized disc, loading the determined DB file from a storage unit storing the DB file and external to the disc, and transmitting information on the loaded DB file to the first controller,
    wherein the first controller controls the operation of the microfluidic system according to operation-related information read from the loaded DB file, and
    wherein the operation-related information comprises operation-related commands and variables of the microfluidic system.

10. The apparatus of claim 9, wherein the DB comprises at least one of fundamental information, work sequence information, detection information, and test information of the disc.

11. The apparatus of claim 9, further comprising an operation unit operating pumps and valves of the microfluidic system,
    wherein the second controller controls the first controller to control an operation of the operation unit by transmitting the operation-related information of the loaded DB file to the first controller.

12. The apparatus of claim 9, further comprising a detector performing detection for a reaction result according to an operation of the microfluidic system,
    wherein the second controller controls the first controller to control detection of the detector by transmitting detection-related information of the loaded DB file to the first controller.

13. The apparatus of claim 12, wherein the detection-related information comprises a detection position and a detection method for the disc in the microfluidic system.

14. The apparatus of claim 12, wherein the detector transmits the detection result value to the second controller via the first controller, and
    the second controller calculates the detection result value according to test-related information of the DB file.

15. The apparatus of claim 14, wherein the test-related information comprises information regarding an analysis result and a calculation method in the microfluidic system.

16. The apparatus of claim 9, wherein the DB has an extensible markup language (XML) format.

17. The apparatus of claim 9, wherein the recognition unit recognizes the disc by using a barcode or radio frequency identification (RFID).

* * * * *